(12) United States Patent
Park et al.

(10) Patent No.: US 8,925,907 B2
(45) Date of Patent: Jan. 6, 2015

(54) VENTILATING APPARATUS, AND METHOD FOR CONTROLLING THE VENTILATING APPARATUS

(75) Inventors: Hyung Ho Park, Changwon-si (KR); Tae Man Yang, Changwon-si (KR); Jeong Hun Kim, Changwon-si (KR)

(73) Assignee: LG Electronics Inc., Seoul (KR)

( * ) Notice: Subject to any disclaimer, the term of this patent is extended or adjusted under 35 U.S.C. 154(b) by 622 days.

(21) Appl. No.: 13/322,841

(22) PCT Filed: May 26, 2010

(86) PCT No.: PCT/KR2010/003324
§ 371 (c)(1),
(2), (4) Date: Nov. 28, 2011

(87) PCT Pub. No.: WO2010/137867
PCT Pub. Date: Dec. 2, 2010

(65) Prior Publication Data
US 2012/0071081 A1    Mar. 22, 2012

(30) Foreign Application Priority Data
May 29, 2009    (KR) ........................ 10-2009-0047441

(51) Int. Cl.
*B01F 3/04*    (2006.01)
*F24F 12/00*   (2006.01)
*A61L 9/16*    (2006.01)
*F24F 3/16*    (2006.01)
*F24F 6/04*    (2006.01)
*C02F 1/02*    (2006.01)
*C02F 1/46*    (2006.01)
*C02F 1/50*    (2006.01)
*F24F 6/00*    (2006.01)

(52) U.S. Cl.
CPC ................ *F24F 12/006* (2013.01); *A61L 9/16* (2013.01); *F24F 3/16* (2013.01); *F24F 6/043* (2013.01); *C02F 1/02* (2013.01); *C02F 1/4608* (2013.01); *C02F 1/505* (2013.01); *C02F 2209/02* (2013.01); *F24F 2003/1664* (2013.01); *F24F 2003/1682* (2013.01); *F24F 2003/1689* (2013.01); *F24F 2006/006* (2013.01); *Y02B 30/16* (2013.01); *Y02B 30/563* (2013.01)
USPC ....................................... 261/107; 261/119.1

(58) Field of Classification Search
CPC .... B01F 3/04; B01F 3/04085; B01F 3/04014; F24F 7/06; F24F 7/08
USPC ................ 261/119.1, 104, 107; 454/251, 252
See application file for complete search history.

(56) References Cited

U.S. PATENT DOCUMENTS

2004/0045909 A1    3/2004    Tomioka et al.

FOREIGN PATENT DOCUMENTS

| EP | 1 434 014 A2 | | 6/2004 |
|----|---|---|---|
| EP | 1 887 287 A2 | | 2/2008 |
| JP | 06323570 A | * | 11/1994 |
| JP | 10-78240 A | | 3/1998 |
| JP | 10-288357 | | 10/1998 |
| JP | 2003-227622 | | 8/2003 |
| JP | 2006234204 A | * | 9/2006 |
| JP | 2007-007053 | | 1/2007 |
| JP | 2009-002612 | | 1/2009 |
| WO | WO 2008/132807 A1 | | 11/2008 |

* cited by examiner

*Primary Examiner* — Robert A Hopkins
(74) *Attorney, Agent, or Firm* — McKenna Long & Aldridge LLP (57) ABSTRACT

The present invention relates to a ventilating apparatus and to a method for controlling the ventilating apparatus. More particularly, the present invention relates to a ventilating apparatus comprising a humidifying unit having an antibiotic function, as well as to a method for controlling the ventilating apparatus.

13 Claims, 9 Drawing Sheets

VENTILATING APPARATUS, AND METHOD FOR CONTROLLING THE VENTILATING APPARATUS

TECHNICAL FIELD

The present invention relates to a ventilating apparatus which includes a humidifying unit having an antibacterial function, and a method for controlling the same.

BACKGROUND ART

The present invention relates to a ventilating apparatus, and a method for controlling the same. More particularly, the present invention relates to a ventilating apparatus which includes a humidifying unit having an antibacterial function, and a method for controlling the same.

In general, the ventilating apparatus is a device for discharging polluted room air and drawing in outdoor fresh and clean air to a room. An air conditioner without a ventilating function cools or heats the room by cooling down or heating up the room air while circulating the room air. Though there are cases when a filter or the like is provided to the air conditioner, since a pollution level of the room increases slowly, and an air cleaning function of the filter or the like has a limitation, a room air ventilating process is required.

Therefore, even in a case the air conditioner is installed for circulating and cooling down or heating up the room air, there are many cases in which the ventilating apparatus is installed, additionally.

Moreover, in order to minimize heat loss in a process of exchanging the cooled/heated room air with outdoor air, a heat exchanger is provided to the ventilating apparatus for heat exchange between the air being drawn from an outside of the room and the air being discharged to an outside of the room to minimize the heat loss which is liable to take place in the ventilating process.

And, by providing a humidifying unit which provides the antibacterial function to the ventilating apparatus, draw-in air being supplied to the room may be humidified.

A humidifying member of the humidifying unit is used wet with water always. If the humidifying function is used intermittently, it is liable that microbes breed at the humidifying member resulting in decomposition of foreign matter having the microbes bred thereon. The breed of the microbes or the decomposition of the foreign matter is likely to pollute the draw-in air being supplied to the room, to produce offensive odor.

DISCLOSURE OF INVENTION

Technical Problem

To solve the problems, an object of the present invention is to provide a ventilating apparatus which includes a humidifying unit having an antibacterial function, and a method for controlling the same.

Technical Solution

To achieve these objects and other advantages and in accordance with the purpose of the invention, as embodied and broadly described herein, a ventilating apparatus includes a ventilating unit having a heat exchanger for making discharge air being discharged from a room to heat exchange with draw-in air being drawn-in from outdoors, an air draw-in fan, and an air discharge fan, a humidifying unit having a water supply tank for holding water, a humidifying member for absorbing water from the water supply tank for the draw-in air to pass therethrough for humidifying the same, and a drain pan for draining the water dropped from the humidifying member, wherein at least one of the water supply tank, the humidifying member, and the drain pan has an antibacterial coating applied thereto, and a submerged discharge sterilizing unit provided to the water supply tank to make selective submerged discharge in the water.

And, the antibacterial coating may be a coating of a mixture or vanadium pentoxide and nano-silver.

In this instance, the submerged discharge sterilizing unit may include at least one discharge cell having one side of a high voltage electrode and the other side of a ground electrode.

And, the high voltage electrode may be a coating of a metallic conductive material on one side of an insulating substrate, and the ground electrode may be a coating of the metallic conductive material on the other side of the insulating substrate.

And, the discharge cell may be provided to an inside surface of the water supply tank.

In this case, the humidifying unit may include a water supply pipe for supplying the water to the water supply tank, and a water supply valve provided on the water supply pipe, wherein the submerged discharge sterilizing unit may be operated for a preset time period after the water supply valve is closed.

And, the water supply tank may include an electric heater provided thereto, for operating for a preset time period after the air draw-in fan is turned off.

In this instance, the water supply tank may include a temperature sensor provided thereto, and the electric heater heats the water in the water supply tank to maintain the water at a temperature higher than a preset temperature for a preset time period.

And, the ventilating apparatus may further include a cooling/heating unit for evaporating or condensing refrigerant to heat or cool the draw-in air being supplied to the humidifying unit.

And, the cooling/heating unit may include a cooling/heating coil having a plurality of fins, and a refrigerant pipe passed through the fins, and an expansion valve.

In another aspect of the present invention, a method for controlling a ventilating apparatus includes a ventilating step for ventilating room air by putting a ventilating unit having an air draw-in fan and an air discharge fan into operation, a humidifying step for supplying water to a water supply tank in a particular section of the ventilating step, and humidifying drawing-in air by making the drawing-in air drawn-in in the ventilating step to pass a humidifying member having the water absorbed therein from the water supply tank, and a water supply tank sterilizing step for sterilizing the water supply tank after the humidifying step is finished.

In this case, the water supply tank sterilizing step may be performed by submerged discharge of the submerged discharge sterilizing unit or water heating of the electric heater provided in the water supply tank.

And, the water supply tank sterilizing step may be performed until water supply tank sterilizing conditions are met, and the sterilized condition may be a preset time or a temperature of the water in the water supply tank.

In this instance, the water temperature may be higher than 80° C.

And, the water supply tank sterilizing step may be performed after the air draw-in fan is turned off or the water supply to the water supply tank is stopped.

Advantageous Effects

The ventilating apparatus and the method for controlling the same of present invention permits to make the room air comfortable by ventilating the room air at the same time with supplying moisture to dry air being introduced to the room.

Moreover, the ventilating apparatus and the method for controlling the same of present invention permit to make hygienic use the humidifying unit provided to the ventilating apparatus.

Moreover, the ventilating apparatus and the method for controlling the same of present invention permit to prevent the water supplied to the humidifying unit from polluting.

Moreover, the ventilating apparatus and the method for controlling the same of present invention permit to prevent offensive odor from occurring, or moderating the offensive odor from the humidifying unit.

BEST MODE

Reference will now be made in detail to the specific embodiments of the present invention, examples of which are illustrated in the accompanying drawings. However, the present invention is not limited to embodiments described herein, but may be embodied in other modes. Rather, the embodiments introduced herein are provided for making contents disclosed herein become complete and perfect and making persons in this field of art to know aspects of the present invention, adequately. Wherever possible, the same reference numbers will be used throughout the drawings to refer to the same or like parts.

Figure 1:
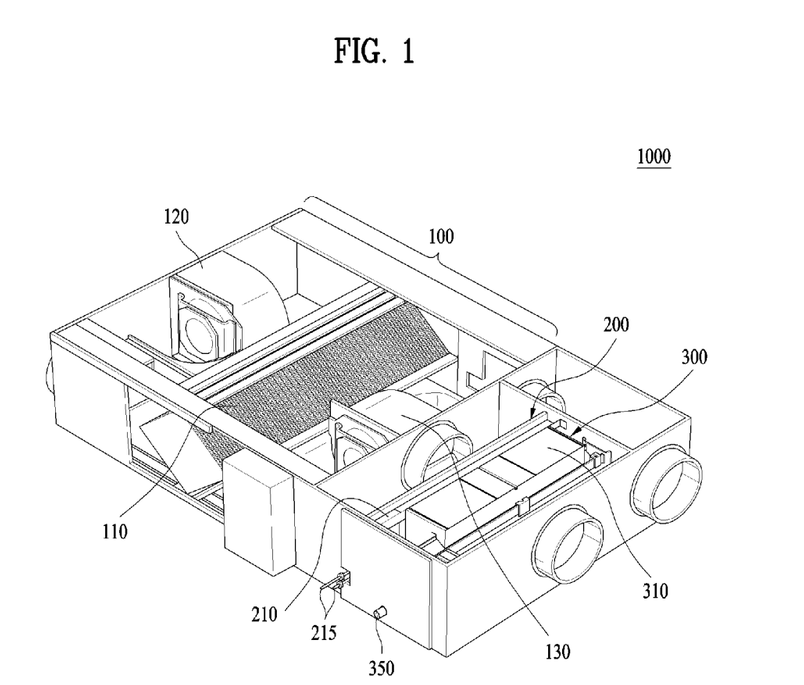
FIG. 1 illustrates a perspective view of a ventilating apparatus in accordance with a preferred embodiment of the present invention.

FIG. 1 illustrates a perspective view of a ventilating apparatus 1000 in accordance with a preferred embodiment of the present invention.

Referring to FIG. 1, the ventilating apparatus may include a ventilating unit 100 having a heat exchanger for making discharge air being discharged from a room to heat exchange with draw-in air being drawn-in from outdoors, an air draw-in fan and an air discharge fan, a humidifying unit 200 having a water supply tank for holding water, a humidifying member for absorbing the water from the water supply tank for the draw-in air to pass therethrough for humidifying the same, and a drain pan for draining the water dropped from the humidifying member, wherein at least one of the water supply tank, the humidifying member, and the drain pan has an antibacterial coating applied thereto, and a submerged sterilizing unit 700 (See FIG. 5) provided to the water supply tank to make selective submerged discharge in the water.

The ventilating apparatus 1000 may include the ventilating unit for exchanging the room air and the outdoor air. And, the ventilating apparatus may include at least one of a cooling/heating unit for heating or cooling the draw-in air being drawn-in through the ventilating unit, and the humidifying unit for humidifying the draw-in air being drawn-in through the ventilating unit. The cooling/heating unit and the humidifying unit can improve comfort requirement of the draw-in air being supplied to the room together with the ventilating unit for enhancing satisfaction of the user.

The ventilating apparatus in FIG. 1 will be described in detail. The ventilating apparatus will be described assuming that the ventilating apparatus includes both the cooling/heating unit and the humidifying unit.

The ventilating unit which is in charge of a ventilating function of the ventilating apparatus may include at least one fan. In the embodiment shown in FIG. 1, the ventilating unit 100 in the ventilating apparatus has an air draw-in fan 130 and an air discharge fan 120. The air draw-in fan and the air discharge fan 120 draw-in the outdoor air and discharge the room air, respectively. The air draw-in fan and the air discharge fan may be positioned at both ends of the ventilating unit 110. The air draw-in fan may be provided to an indoor side end of the ventilating unit 110 and the air discharge fan 120 may be provided to an outdoor side end of the ventilating unit 110.

The heat exchanger which makes the air being drawn-in to heat exchange with the air being discharged may be provided between the air draw-in fan 130 and the air discharge fan 120. The heat exchanger 110 makes the air being drawn-in to heat exchange with the air being discharged for enabling to prevent a temperature of the room air from changing sharply, and to reduce an air conditioning load of the room.

For an example, if it is assumed that a ventilating process is performed in a room cooling process, to discharge cooled room air and to draw-in warm outdoor air, a room cooling load (The air conditioning load) of the air conditioner or the like increases.

Therefore, by making the air being drawn-in to heat exchange with the air being discharged at the heat exchanger 110, the cooling load or the heating load can be reduced, and a temperature variation the user feels can be reduced. A detailed structure of the heat exchanger 110 will be described, later.

Each of the air draw-in fan 130 and the air discharge fan 120 may be a cross flow fan, and the heat exchanger 110 may be arranged between the air draw-in fan 130 and the air discharge fan 120.

The air draw-in fan 130 serves to blow the outdoor air (Drawn-in air) passed through the heat exchanger 110 toward the cooling/heating unit 200 which will be described later, and the air discharge fan 120 serves to discharge the room air (Discharge air) passed through the heat exchanger 110 to outdoors.

The draw-in air drawn-in by the air draw-in fan 130 may be blown toward the cooling/heating unit 200. The cooling/heating unit 200 includes a cooling/heating coil 210 for cooling or heating the draw-in air passing therethrough with evaporated or condensed refrigerant, and an expansion valve (Not shown) for blocking or expanding the refrigerant, selectively.

The cooling/heating coil 210 in the cooling/heating unit 200 may have a plurality of fins 213, and a refrigerant pipe 215 passed through the fins.

The refrigerant being supplied to the cooling/heating coil may be supplied from an outdoor unit of the air conditioner provided separate from the ventilating apparatus.

Of course, though it is possible that the ventilating apparatus has a compressor and the heat exchanger in the ventilating apparatus, in order to reduce a volume of the ventilating apparatus, minimize noise, and increase cooling and heating efficiency, the refrigerant may be supplied from the outdoor unit of the air conditioner installed at outdoors. The cooling/heating coil of the cooling/heating unit 200 will be described in detail, later.

The ventilating apparatus may include the humidifying unit 300 in rear of the cooling/heating unit 200, additionally. The humidifying unit 300 may include a humidifying member for humidifying the air passed therethrough by absorbing the water and letting the water to flow down, which will be described in detail, later.

Figure 2:
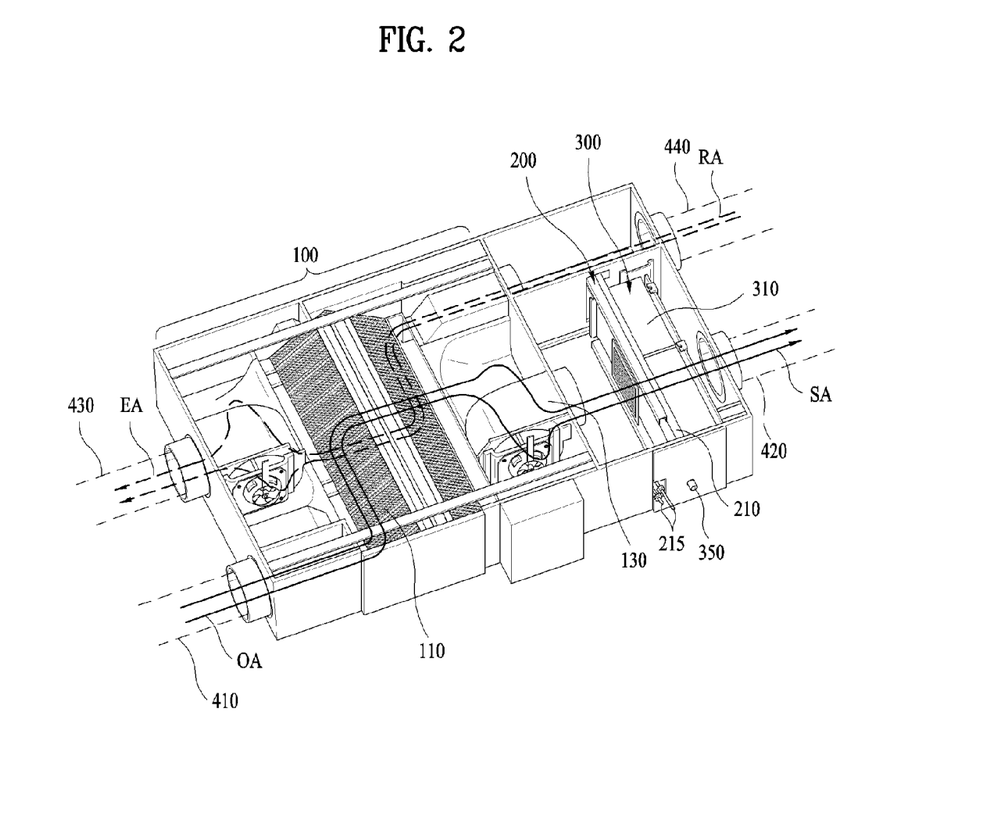
FIG. 2 illustrates a perspective view of the ventilating apparatus in FIG. 1 seen from another angle.

FIG. 2 illustrates a perspective view of the ventilating apparatus in FIG. 1 seen from another angle. The ventilating apparatus draws-in or discharges the room air through an inlet (Not shown) which draws-in the room air from the room, and an outlet (Not shown) which discharges the room air.

A process for drawing-in the room air and discharging the room air through the ventilating apparatus is made by first and second air discharge ducts 430 and 440 respectively connected to the ventilating apparatus, and a process for drawing-in the outdoor air and drawing-in the outdoor air through the ventilating apparatus is made by first and second air draw-in ducts 410 and 420 respectively connected to the ventilating apparatus.

The draw-in air OA drawn-in through the first air draw-in duct 410 is heat exchanged at the heat exchanger in a draw-in unit 100, cooled or heated at the cooling/heating coil 210 of the cooling/heating unit 200, humidified at the humidifying unit 300, and supplied to the room SA.

The humidifying unit 300 can make the room comfortable by dropping a temperature and elevating humidity of the draw-in air heated at the cooling/heating unit 200 in winter. That is, it is easy to humidify the air heated at the cooling/heating unit 200 at the humidifying unit 300. Therefore, the humidifying unit 300 is meaningful in dropping the temperature and elevating the humidity of the dry and heated air in a heating mode.

Opposite to this, the room air RA drawn-in from the room does not pass, but goes around the cooling/heating unit 200, is heat exchanged at the heat exchanger 110 in the ventilating unit 100, and discharged to the outdoors EA.

FIG. 3A illustrates a perspective view of a heat exchanger unit 110 in a ventilating unit 100 of the ventilating apparatus. And, FIG. 3B illustrates a perspective view of a cooling/heating coil 210 in a cooling/heating unit 210 of the ventilating apparatus.

Referring to FIG. 3A, the heat exchanger 110 may have an alternated stack of flat plates 113 and corrugated plates 114. The corrugated plates 114 may be arranged to cross the flat plates 113 perpendicular thereto with the flat plates 113 disposed therebetween.

The heat exchanger 110 forms a first flow passage 115 and a second flow passage 116 with to the stack of the flat plates 113 and the corrugated plates 114. The first flow passage 115 and the second flow passage 116 are passages perpendicular to each other.

The flat plates 113 or the corrugated plates 114 of the heat exchanger 110 may have an adsorbing material coated on a surface thereof for adsorbing water vapor. The adsorbing material may be, for an example, silica gel, zeolite, ion exchange resin, and so on.

Moreover, the flat plates 113 or the corrugated plates 114 of the heat exchanger 110 may be formed of a thin film material and have the adsorbing material coated on a surface thereof such that the air passing through the first flow passage 115 and the second flow passage 116 can be made to exchange heat as well as moisture.

That is, in a case the discharge air RA supplied from the room flows the first flow passage 115 and the draw-in air OA drawn-in from the outdoor flows the second flow passage 116, adsorbent adsorbs the moisture from the first flow passage 115 and supplies the moisture to the draw-in air OA in the second flow passage 116 to elevate humidity of the draw-in air OA. Thus, though a humidifying process may be performed by the humidifying unit 300 if the humidifying unit 300 is provided to the ventilating apparatus, even in a case the humidifying unit 300 is not provided, a difference of humidity between the draw-in air OA and the discharge air RA can be reduced, primarily.

Figure 3:
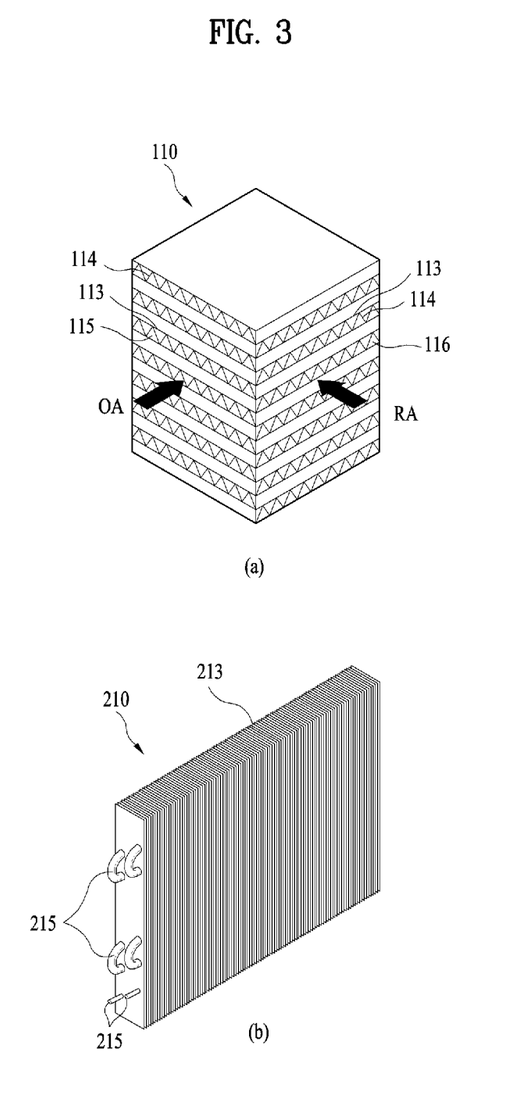
FIG. 3A illustrates a perspective view of a heat exchanger unit in a ventilating unit of the ventilating apparatus.
FIG. 3B illustrates a perspective view of a cooling/heating coil in a cooling/heating unit of the ventilating apparatus.

FIG. 3B illustrates a perspective view of a cooling/heating coil 210 in a cooling/heating unit 200 of the ventilating apparatus. The cooling/heating coil 210 may be a cross fin type Fin-Tube heat exchanger. The cooling/heating coil 210 may include a plurality of rectangular fins 213 of metal, such as aluminum, and a refrigerant pipe 215 passed through the fins 213. And, though not shown in FIG. 3, an expansion valve (Not shown) may be provided to the cooling/heating coil 210 for selective supply of refrigerant to the cooling/heating coil 210. The expansion valve may be an Electric Expansion Valve EEV, or the like. The expansion valve can perform to serve to cut-off or supply the refrigerant selectively, or to expand the refrigerant introduced to the cooling/heating coil 210.

Therefore, in a case of room cooling, the cooling/heating coil 210 can be operative as an evaporator, and, in a case of room heating, the cooling/heating coil 210 can be operative as a condenser.

Since the ventilating apparatus may be difficult to provide an adequate cooling/heating function alone, the ventilating apparatus may be operated in association with an additional air conditioner. If the ventilating apparatus has no compressor provided therein, the ventilating apparatus may have the refrigerant supplied thereto from the outdoor unit of the air conditioner.

Figure 4:
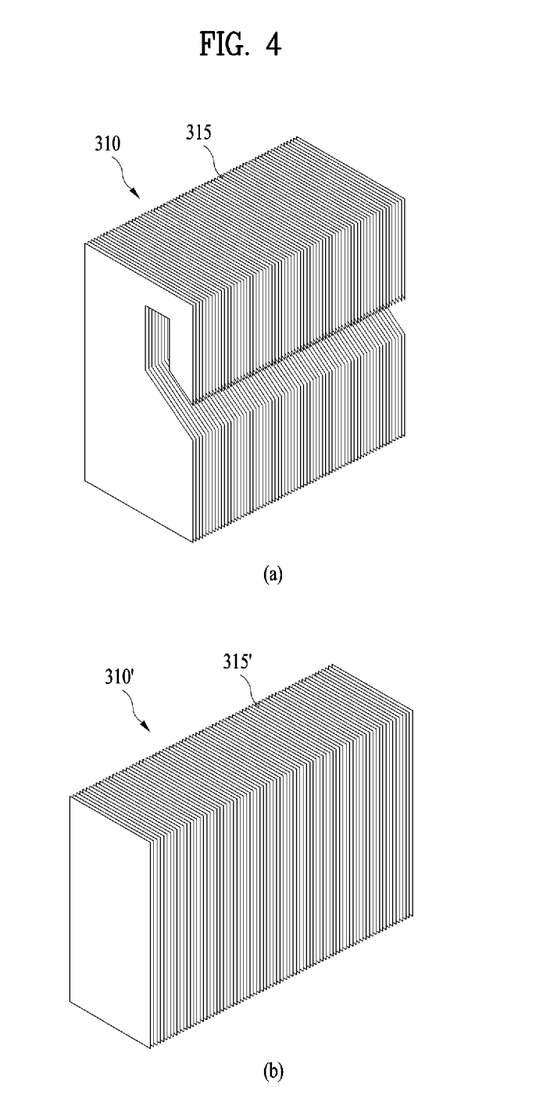
FIGS. 4A and 4B illustrate perspective views of humidifying members of a ventilating apparatus in accordance with preferred embodiment of the present invention, respectively.

FIGS. 4A and 4B illustrate perspective views of humidifying members of a ventilating apparatus in accordance with preferred embodiment of the present invention respectively, wherein FIG. 4A illustrates a perspective view of a humidifying member 310, and 310' having a bent portion on an upper side, and FIG. 4B illustrates a perspective view of a humidifying member of a hexahedral shape.

The humidifying member illustrated in FIGS. 4A and 4B may perform humidification by absorbing water and letting the draw-in air pass between the humidifying member having the water absorbed therein thus.

The humidifying member 310 may be a stack of a plurality of water absorbing material sheets 315 or 315'. The water absorbing material sheets 315 or 315' of non-woven fabric or the like makes the water absorbed in the humidifying member 310 or 310' to move down while flowing down along a surface of the humidifying member 310 or 310' or being absorbed in the water absorbing material sheets 315 or 315'.

And, the humidifying member may have a portion (Not shown) extended from a top side and bent downward from the extension.

The humidifying member 310 or 310' absorbs the water and lets the water to flow downward, while passing the drawn-in air from outdoors therethrough to humidify the drawn-in air.

Figure 5:
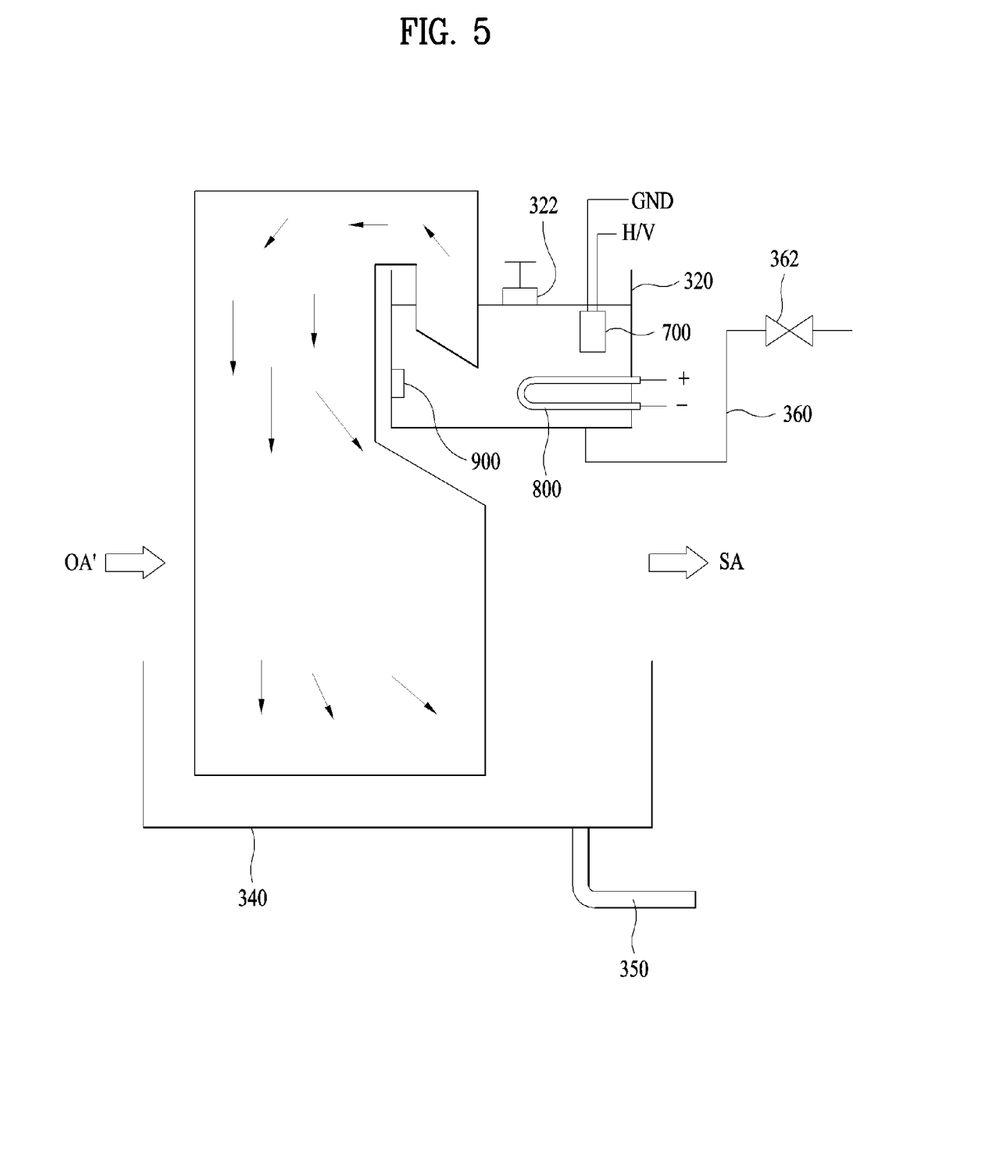
FIG. 5 illustrates a schematic view of a humidifying unit and a water supply unit in a ventilating apparatus in accordance with preferred embodiment of the present invention.

FIG. 5 illustrates a schematic view of a humidifying unit and a water supply unit in a ventilating apparatus in accordance with preferred embodiment of the present invention.

The humidifying unit 300 further includes a water supply pipe 360 for supplying the water to the water supply tank 340, and a water supply valve 362 provided to the water supply pipe 360, and the submerged discharge sterilizing unit 700 provided to an inside of the water supply tank 340 (By attaching to an inside surface or the like) can be operated for a preset time period after the water supply valve 362 is closed. A reason why the submerged discharge sterilizing unit 700 is operated after the water supply valve is closed will be described, later.

For conveniences' sake, a case will be described, in which the humidifying member shown in FIG. 4A is used. The bent portion 312 on an upper side of the humidifying member 310 is extended down to the water supply tank 320 provided under the humidifying member 310 for absorbing the water from the water supply tank 320. The water is supplied to the water supply tank 320 through the water supply pipe 360 connected to the water supply tank 320 and the water supply valve 362 which may cut-off the water being supplied from the water supply pipe 360, selectively.

A water level of the water supply tank 320 may be detected with a water sensor 322, for an example, a float switch. The water in the water supply tank has the water supplied from the water supply tank 360, and is provided with the water supply valve 362 for selective cutting off of the water supply from the water supply pipe.

The water supply valve 362 is closed/opened by a control unit 600 of the ventilating apparatus according to a water level measured by the water sensor 322, selectively. And, the humidifying unit 300 is provided with the drain pan 340 for draining the water which is absorbed in the humidifying unit 300, and not vaporizes, but drops. The drain pan 340 may be provided with a draining pipe 350, additionally.

The humidifying unit of the ventilating apparatus of the present invention lets the water absorbed from the water supply tank 320 to flow down from a surface of the humidifying member, and enables the draw-in air to pass therethrough to humidify the draw-in air.

Therefore, since bacteria or microbes are likely to breed at the flow passage in which the water is stored and supplied, an antibacterial coating may be applied to at least one of the water supply tank 320, the humidifying member 310, and the drain pan 340 for preventing the bacteria from breeding. The antibacterial coating may be a coating of a mixture of vanadium pentoxide and nano-silver.

A coating material used for the antibacterial coating may be nano-silver Ag and/or vanadium pentoxide $V_2O_5$. Though the nano-silver Ag and/or vanadium pentoxide $V_2O_5$ have the antibacterial function, if the nano-silver Ag and vanadium pentoxide $V_2O_5$ is used together, the antibacterial or sterilizing function can be maximized, and pollution can be reduced, to improve a lifetime.

The vanadium pentoxide $V_2O_5$ is also called as vanadic anhydride. The vanadium pentoxide $V_2O_5$ is orange colored powder with a melting point of 690° C., and density of 3.375 (18° C.). The vanadium pentoxide $V_2O_5$ does not dissolve in water, but in alkali to form vanadate. The vanadium pentoxide $V_2O_5$ dissolves in strong acid, and is amphoteric oxide. The vanadium pentoxide $V_2O_5$ is prepared by heating vanadium powder in air, or thermal decomposition of $NH_4VO_3$. The vanadium pentoxide $V_2O_5$ is used as a catalyst in preparation of sulfuric acid by a contact process, and is a material known to have antibacterial/sterilizing functions.

Accordingly, the nano-silver Ag and/or vanadium pentoxide $V_2O_5$ may be coated for the antibacterial/sterilizing functions together or individually, to maximize the antibacterial/sterilizing functions by interaction.

The water supply tank 320 is provided with the submerged discharge sterilizing unit 700 for sterilizing or disinfecting the water supply tank. The submerged discharge sterilizing unit 700 sterilizes or disinfects the water supply tank. Detailed configuration and effect of the submerged discharge sterilizing unit 700 will be described, later. Though FIG. 5 illustrates the submerged discharge sterilizing unit 700 having one discharge cell, a number of the discharge cells may vary with a size of the water supply tank 320. In this instance, the discharge cell of the submerged discharge sterilizing unit 700 may be provided to an inside surface of the water supply tank 320.

And, the water supply tank 320 may have an electric heater 800 provided thereto additionally for sterilizing or disinfecting the water supply tank 320. The electric heater 800 may heat the water held in the water supply tank 320 for preventing the bacteria from breeding.

The water supply tank 320 may have a temperature sensor 900 provided in the water supply tank 320 for measuring a temperature of the water in the water supply tank 320 heated by the electric heater 800. The temperature sensor 900 may be mounted to the water supply tank in an assumption that the electric heater 800 is provided to the water supply tank.

A detailed sterilizing or disinfecting method of the water supply tank 320 with the submerged discharge sterilizing unit 700 and the electric heater 800 will be described, later.

Both the submerged discharge sterilizing unit 700 and the electric heater 800 or either one thereof may be provided to the water supply tank 320.

Figure 6:
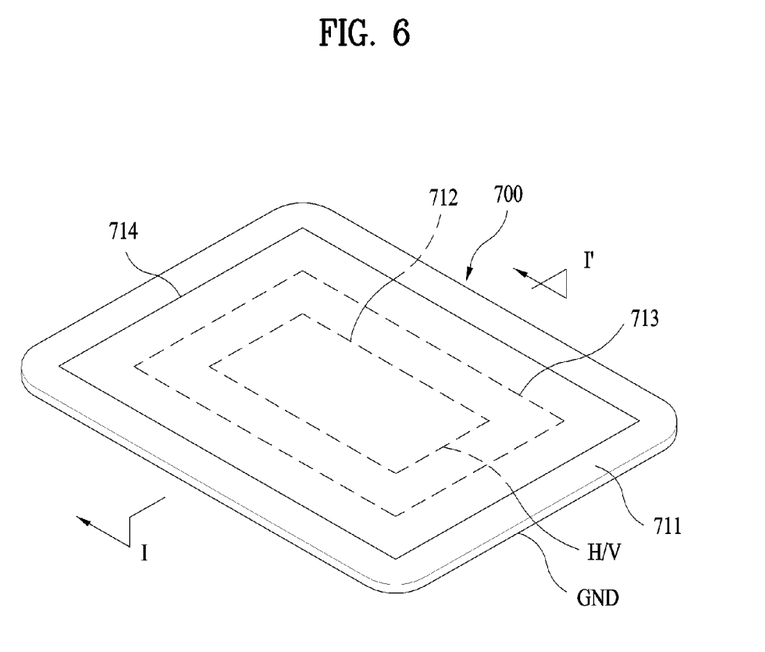
FIG. 6 illustrates an exterior perspective view of the submerged discharge sterilizing unit and FIG. 7 illustrates a section across a line I-I' in FIG. 6.
Figure 7:
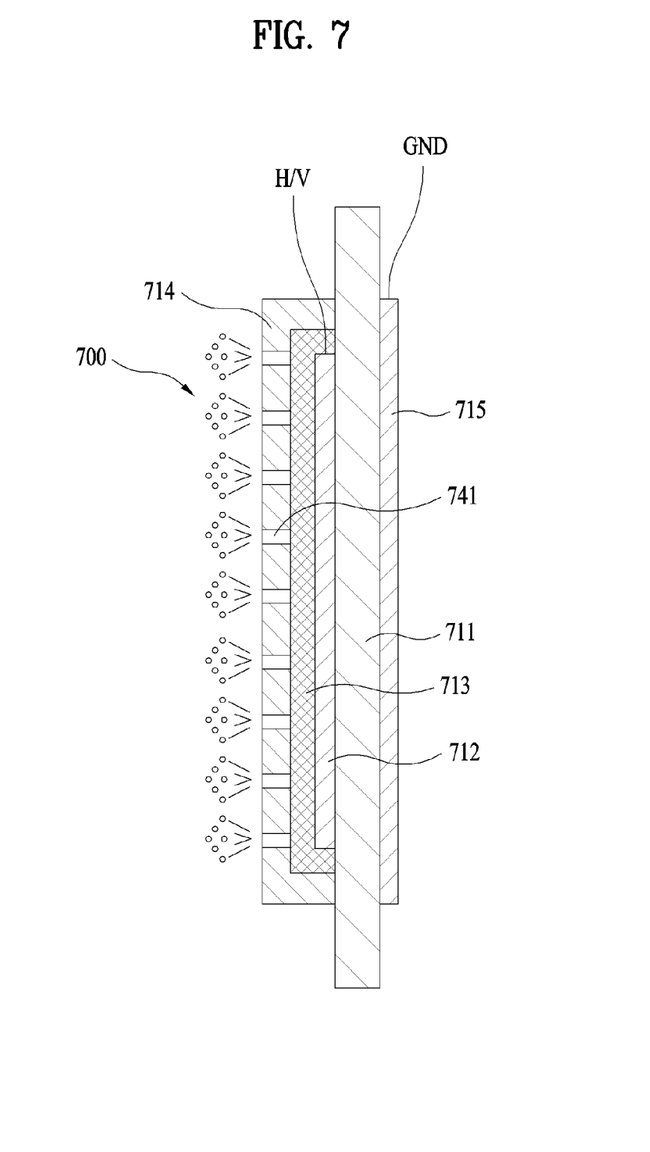

FIG. 6 illustrates an exterior perspective view of the submerged discharge sterilizing unit and FIG. 7 illustrates a section across a line I-I' in FIG. 6.

Referring to FIGS. 6 and 7, the submerged discharge sterilizing unit 700 in accordance with a preferred embodiment of the present invention has a rectangular shape and may be detachably mounted to one side of the water supply valve. The submerged discharge sterilizing unit 700 may be provided with at least one discharge cell having one side of a high voltage electrode and the other side of a ground voltage electrode. That is, one side of the submerged discharge sterilizing unit 700 is a high voltage electrode surface H/V and the other side thereof is an opposite electrode, i.e., a ground electrode surface GND.

The high voltage electrode surface of the discharge cell may be formed by coating a metallic conductive material on one side of an insulating substrate, and the ground electrode surface may be formed by coating the metallic conductive material on the other side of the insulating substrate.

In detail, the discharge cell of the submerged discharge sterilizing unit 700 in accordance with a preferred embodiment of the present invention includes an insulating substrate 711 of a ceramic material, a high voltage electrode portion 712 provided to a high voltage electrode surface of the insulating substrate 711, a ground electrode portion 715 provided to a ground electrode surface, a first insulating layer 713 for preventing the high voltage electrode portion 712 from oxidizing as the high voltage electrode portion 712 is brought into contact with water, and a second insulating layer 714 provided to a surface of the first insulating layer 713.

In more detail, the insulating substrate 711 cuts-off electric conduction between the high voltage electrode portion 712 and the ground electrode portion 715, and functions as a dielectric provided between the two electrodes. Therefore, besides the ceramic material, the insulating substrate 711 may also be formed of tempered glass.

As described before, the high voltage electrode portion 712 has the metallic conductive material coated on a surface of the insulating substrate 711 in micron thickness. And, the conductive metallic material of the high voltage electrode portion 712 has silver Ag included thereto. Besides the silver, though platinum or nickel is viable, the embodiment will be described taking a case in which the silver which is favorable in view of a production cost is used.

And, the ground electrode portion 715 also has the metallic conductive material coated on the other surface of the insulating substrate 711 in a thin film entirely or partially. And, the high voltage electrode portion 712 and the ground electrode portion 715 have power lines connected thereto for applying power thereto, and for applying the high voltage thereto through the power line connected to the ground electrode portion 715, momentarily.

And, in order to prevent the high voltage electrode portion 712 from oxidizing as the high voltage electrode portion 712 is brought into contact with the water, the high voltage electrode portion 712 has the first insulating layer 713 of a coat of ruthenium oxide $RuO_2$ on a surface thereof. And, in order to enhance an insulating performance of the high voltage electrode portion 712, the high voltage electrode portion 712 has the second insulating layer 714 of a coat of glass powder, additionally.

In more detail, the second insulating layer 714 of a coated film has micron pores 741 formed therein for forming a plurality of micron bubbles through the pores 741 upon application of the voltage to the high voltage electrode portion 712. And, as a number of the micron bubbles increase, electric discharge occurs at the portion.

Upon application of the voltage to the high voltage electrode portion 712 in a state the discharge cell of the submerged discharge sterilizing unit 700 is submerged in the water supply tank 320, a large number of micron bubbles are formed in the vicinity of the pores 741 in the second insulating layer 714. And, if the electric discharge occurs among the micron bubbles, large numbers of radicals, i.e., hydroxyl group and active oxygen, are produced. And, of the large numbers of radicals, some of the hydroxyl group re-couple, to produce oxygen peroxide. And, the radicals remove the bacteria and the microbes from the water.

Since the submerged discharge sterilizing unit 700 is very small and thin, the submerged discharge sterilizing unit 700 may be mounted to small domestic appliances, easily. And, since the high voltage electrode and the ground electrode are formed as one unit, mounting of the submerged discharge sterilizing unit 700 is easy.

Figure 8:
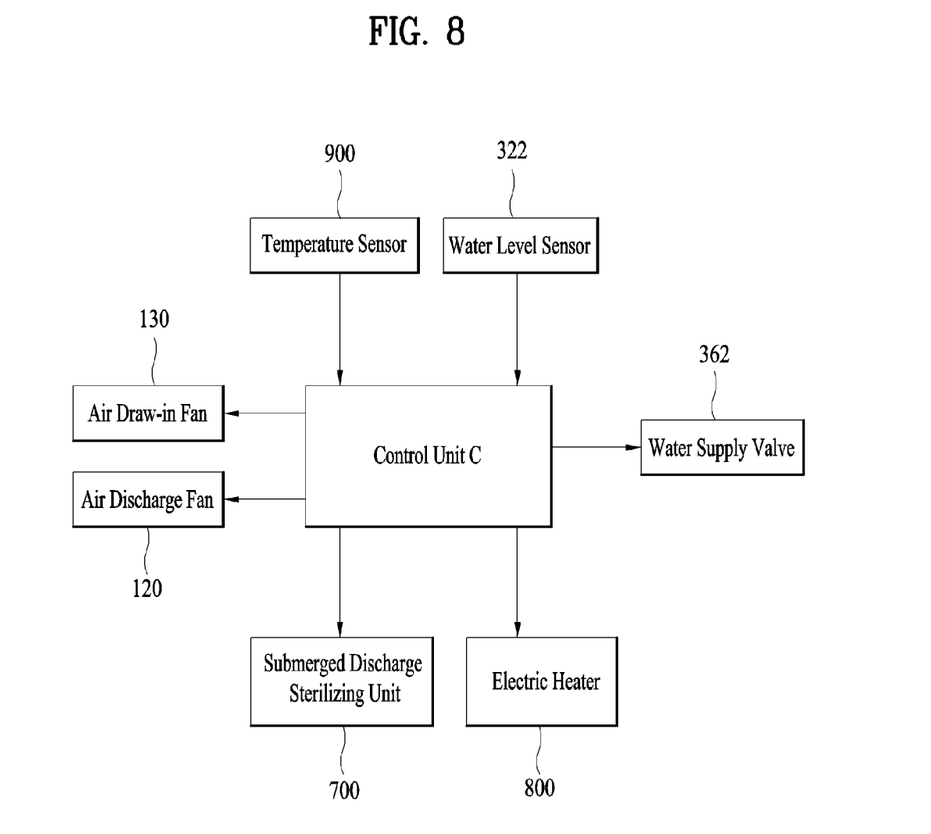
FIG. 8 illustrates a block diagram of a humidifying unit in a ventilating apparatus in accordance with preferred embodiment of the present invention.

Accordingly, since a size of the submerged discharge sterilizing unit 700 can be minimized, the submerged discharge sterilizing unit 700 may be mounted to the inside of the water supply tank 320 for removing the bacteria and virus liable to breed in the water supply tank 320. FIG. 8 illustrates a block diagram of a humidifying unit in a ventilating apparatus in accordance with preferred embodiment of the present invention. The cooling/heating unit 200 which cools or heats the draw-in air being supplied from the ventilating unit 100 will not be described.

The control unit C of the ventilating apparatus may use the water level and the water temperature of the water in the water supply tank measured with the temperature sensor 900 and the water level sensor 322 mounted in the water supply tank 320 as control information on the ventilating apparatus.

The control unit C of the ventilating apparatus controls the air discharge fan 120 and the air draw-in fan 130 of the ventilating unit 100 to control room ventilating operation, and controls the water supply valve 362 on the water supply pipe 360, to control whether a humidifying function is to be activated or not on the assumption that the ventilating operation is to be performed.

That is, if the control unit C controls the water supply valve 362 to supply the water to the water supply tank 320 while the ventilating operation is performed, the humidifying member absorbs the water above a certain level to humidify the draw-in air passing therethrough.

And, the control unit C of the ventilating apparatus controls the submerged discharge sterilizing unit 700 or the electric heater 800 mounted to the water supply tank 320.

Figure 9:
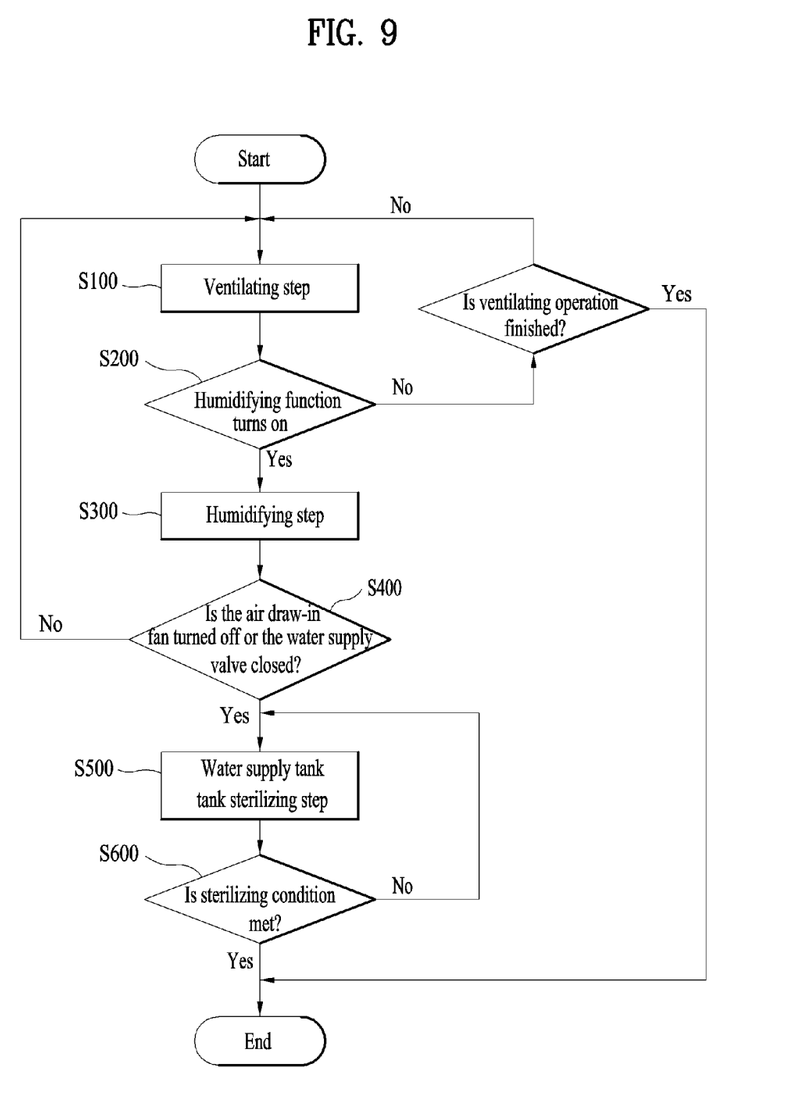
FIG. 9 illustrates a flow chart showing the steps of a method for controlling a ventilating apparatus in accordance with preferred embodiment of the present invention.

FIG. 9 illustrates a flow chart showing the steps of a method for controlling a ventilating apparatus in accordance with preferred embodiment of the present invention.

Referring to FIG. 9, the method for controlling a ventilating apparatus, at large, includes a ventilating step S100 for ventilating room air by putting a ventilating unit having an air draw-in fan and an air discharge fan into operation, a humidifying step S200 for supplying water to a water supply tank in a particular section of the ventilating step, and humidifying drawing-in air by making the drawing-in air drawn-in in the ventilating step to pass a humidifying member having the water absorbed therein from the water supply tank, and a water supply tank sterilizing step S300 for sterilizing the water supply tank after the humidifying step is finished.

The ventilating step S100 may be performed by putting the air draw-in fan 130 and the air discharge fan 120 of the ventilating unit 100 into operation.

And, since the humidifying step S200 is performed while the draw-in air passes through the humidifying member in an assumption that the ventilating step S200 is performed, if no separate damper member is provided, turn on/off control of a humidifying function may be made by closing and opening of the water supply valve 362 on the water supply pipe 360. Therefore, if the water level of the water supply tank 320 drops for the humidifying member unable to absorb the water, the humidifying function may be controlled to be turned off.

Though the water supply tank sterilizing step S300 in the method for controlling a ventilating apparatus of the present invention may be performed before operation of the ventilating apparatus, it is preferable that the water supply tank sterilizing step S300 is performed after the ventilating function or the humidifying function is finished.

The water supply tank sterilizing step S300 may be performed by submerged discharge of the submerged discharge sterilizing unit 700 or water heating of the electric heater provided in the water supply tank.

As described before, it is preferable that the submerged discharge sterilizing unit is put into operation for a preset time period after the water supply valve is closed.

Since the sterilizing of the submerged discharge sterilizing unit 700 is required to be continuous for a fixed time period (For an example, 20 minutes), it is preferable that the water supply tank sterilizing step S300 is performed after the ventilating operation or the humidifying operation is finished (Turn off of the air draw-in fan and so on or closure of the water supply valve) for the submerged discharge sterilizing unit 700 or the electric heater to perform the sterilization for an adequate time period.

And, it is also preferable that the electric heater 800 in the water supply tank is operated for a preset time period after the ventilating operation or the humidifying operation is finished (Turn off of the air draw-in fan and so on or closure of the water supply valve).

In this instance, it is preferable that the water supply tank is provided with the temperature sensor, and the electric heater heats the water in the water supply tank such that the water temperature is maintained at a temperature higher than a preset temperature for a preset time period.

Therefore, in a step S400 of determining whether the ventilating operation or the humidifying operation is finished or not after the humidifying function is selected to start the humidifying operation, turn off of the air draw-in fan 130 or closure of the water supply valve 362 may be determined.

Since it can be determined that the ventilating operation or the humidifying operation is finished if the air draw-in fan 130 is turned off or the water supply valve 362 is closed after the humidifying operation, the water supply tank sterilizing step S300 may be performed.

The water supply tank sterilizing step S300 is performed, and a sterilized condition determining step S600 is performed for determining whether various sterilizing conditions are met or not. The water supply tank sterilizing step S300 is performed until water supply tank sterilizing conditions are met. The sterilized condition may be a preset time or the temperature of the water in the water supply tank.

Therefore, if the submerged discharge sterilizing unit 700 is used, whether a fixed time is passed or not is determined, and if the water is heated with the electric heater 800, whether the water temperature in the water supply tank is reached to a preset temperature or kept for a preset time period or not is determined.

For an example, if the submerged discharge sterilizing unit 700 is used, it may be determined that whether the discharge is kept for more than about 20 minutes or not, and, if the electric heater 800 is used, it may be determined that whether the water temperature is maintained at a temperature over 80 degrees for more than 10 minutes or not. Of course, since the condition of maintaining the water temperature at a temperature over 80 degrees for more than 10 minutes is one example of the sterilized condition, the condition may vary with regions or environments in which the ventilating apparatus is used.

If it is determined that the sterilizing conditions are met in the sterilized condition determining step S600, operation of the ventilating apparatus may be turned off, entirely.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

The invention claimed is:

1. A ventilating apparatus comprising:
    a ventilating unit having a heat exchanger exchanging heat from drawn-in air from outdoors prior to discharging air, a draw-in fan, and a discharge fan;
    a humidifying unit having a water supply tank for holding water, a humidifying member absorbing the water from the water supply tank and humidifying the drawn-in air, and a drain pan for draining the water dropped from the humidifying member, wherein at least one of the water supply tank, the humidifying member, and the drain pan has an antibacterial coating applied thereto; and
    a sterilizing unit in the water supply tank to sterilize water in the water supply tank,
    wherein the sterilizing unit includes:
        a discharge cell having a high voltage electrode on a first side and a ground electrode on a second side; and
        an insulating layer on a surface of the high voltage electrode for preventing the high voltage electrode from contacting water.

2. The ventilating apparatus as claimed in claim 1, wherein the antibacterial coating is selected from the group consisting of vanadium pentoxide, nano-silver, and a mixture of vanadium pentoxide and nano-silver.

3. The ventilating apparatus as claimed in claim 1, wherein the high voltage electrode is a coating of a metallic conductive material on one side of an insulating substrate, and the ground electrode is a coating of the metallic conductive material on a different side of the insulating substrate.

4. The ventilating apparatus as claimed in claim 3, wherein the discharge cell is on an inside surface of the water supply tank.

5. The ventilating apparatus as claimed in claim 1, wherein the humidifying unit further includes;
    a water supply pipe for supplying the water to the water supply tank, and
    a water supply valve on the water supply pipe,
    wherein the sterilizing unit is operated for a preset time period after the water supply valve is closed.

6. The ventilating apparatus as claimed in claim 1, wherein the water supply tank includes an electric heater for operating for a preset time period after the draw-in fan is turned off.

7. The ventilating apparatus as claimed in claim 6, wherein the water supply tank further includes a temperature sensor, and the electric heater heats the water in the water supply tank to maintain the water at a temperature higher than a preset temperature for a preset time period.

8. The ventilating apparatus as claimed in claim 1, further comprising a cooling/heating unit for evaporating or condensing refrigerant to heat or cool the draw-in air supplied to the humidifying unit.

9. The ventilating apparatus as claimed in claim 8, wherein the cooling/heating unit comprises:
    a cooling/heating coil having a plurality of fins;
    a refrigerant pipe passed through the fins; and
    an expansion valve.

10. A method for controlling a ventilating apparatus comprising a ventilating unit, a humidifying unit having a water supply tank, and a sterilizing unit in the water supply tank, the sterilizing unit having a discharge cell where one side is a high voltage electrode and a different side is a ground electrode with an insulating layer on a surface of the high voltage electrode for preventing the high voltage electrode from contacting with water, the method comprising:
    a ventilating step for ventilating room air by operating a ventilating unit having a draw-in fan and a discharge fan;
    a humidifying step for supplying water to a water supply tank, and humidifying drawn-in air by passing the drawn-in air through a humidifying member having absorbed water from the water supply tank; and
    a water sterilizing step for sterilizing the water in the water supply tank after the humidifying step is finished,
    wherein the water sterilizing step is performed by discharge of the sterilizing unit.

11. The method as claimed in claim 10, wherein the water sterilizing step is performed until a water sterilizing condition is met, and the sterilizing condition is a preset time or a temperature of the water.

12. The method as claimed in claim 11, wherein the water temperature is higher than 80° C.

13. The method as claimed in claim 10, wherein the water sterilizing step is performed after the draw-in fan is turned off or a water supply to the water supply tank is stopped.

* * * * *